US012767970B2

(12) United States Patent
Lampel et al.

(10) Patent No.: US 12,767,970 B2
(45) Date of Patent: Oct. 20, 2026

(54) METHODS AND COMPOSITIONS FOR MELANIN SYNTHESIS

(71) Applicant: RAMOT AT TEL AVIV UNIVERSITY LTD., Tel Aviv (IL)

(72) Inventors: Ayala Lampel, Tel Aviv (IL); Tlalit Massarano, Tel Aviv (IL); Avigail-Elah Baruch Leshem, Tel Aviv (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 445 days.

(21) Appl. No.: 18/209,263

(22) Filed: Jun. 13, 2023

(65) Prior Publication Data

US 2024/0002895 A1 Jan. 4, 2024

Related U.S. Application Data

(63) Continuation of application No. PCT/IL2022/050003, filed on Jan. 2, 2022.

(60) Provisional application No. 63/134,789, filed on Jan. 7, 2021.

(51) Int. Cl.
*C12P 21/02* (2006.01)

(52) U.S. Cl.
CPC .................................... *C12P 21/02* (2013.01)

(58) Field of Classification Search
None
See application file for complete search history.

(56) References Cited

U.S. PATENT DOCUMENTS

| | | | | |
|---|---|---|---|---|
| 4,855,144 | A | 8/1989 | Leong et al. | |
| 2011/0097385 | A1* | 4/2011 | Sabetsky | A61P 5/50 424/490 |
| 2012/0021029 | A1 | 1/2012 | Garcia Sanz et al. | |
| 2014/0356283 | A1 | 12/2014 | Cheng et al. | |
| 2018/0369115 | A1 | 12/2018 | Alminana Domenech et al. | |
| 2019/0187031 | A1* | 6/2019 | Johnson-Buck | C07K 1/14 |
| 2020/0215208 | A1* | 7/2020 | Ju | A61K 49/12 |

FOREIGN PATENT DOCUMENTS

WO 2004018066 A2 3/2004

OTHER PUBLICATIONS

Mayer et al., Biologically Active Molecules with a "Light Switch", Jul. 20, 2006 (Year: 2006).*
Hansen et al (2015) Wavelength-selective cleavage of photoprotecting groups: strategies and applications in dynamic systems, Chem. Soc. Rev. 44, pp. 3358-3377, DOI: 10.1039/c5cs00118h.
Cakmak & Keating (2016) Combining Catalytic Microparticles with Droplets Formed by Phase Coexistence: Adsorption and Activity of Natural Clays at the Aqueous/Aqueous Interface, Scientific Reports 7:3215, DOI: 10.1038/s41598-017-03033-z.
Chou et al (2010) Photocaged T7 RNA Polymerase for the Light Activation of Transcription and Gene Function in Pro- and Eukaryotic Cells, ChemBioChem 11:972-977. DOI: 10.1002/cbic.201000041.
Schneider et al (2018) Synthesis of a Photo-Caged DOPA Derivative by Selective Alkylation of 3,4-Dihydroxybenzaldehyde, Eur. J. Org. Chem., pp. 2053-2063. DOI: 10.1002/ejoc.201701749.
Massarano et al (2020) Spatiotemporal Control of Melanin Synthesis in Liquid Droplets, Communication, doi: 10.1021/acsami.1c21006.
Solano, F (2014) Melanins: Skin Pigments and Much More—Types, Structural Models, Biological Functions, and Formation Routes, Hindawa Publications, New Journal of Science, vol. 2014 Article ID 498276, http://dx.doi.org/10.1155/2014/498276.
PCT International Search Report for International Application No. PCT/IL2022/050003, mailed Apr. 7, 2022, 3pp.
PCT Written Opinion for International Application No. PCT/IL2022/050003, mailed Apr. 7, 2022, 6pp.

* cited by examiner

*Primary Examiner* — Genevieve S Alley
(74) *Attorney, Agent, or Firm* — The Roy Gross Law Firm, LLC; Roy D. Gross

(57) ABSTRACT

The invention relates to a composition comprising a polymer—based droplet, wherein the polymer—based droplet comprises one or more of melanin, a tyrosine substrate with a cleavable protecting group on the side chain, tyrosine, tyrosinase and any combination thereof. The composition further relates to a method of synthesizing melanin comprising the steps of: obtaining a polymer—based droplet containing a tyrosine substrate with a cleavable protecting group on the side chain (protected tyrosine) or a polymer—based droplet containing tyrosine (unprotected); wherein the tyrosine is oxidized by tyrosinase and polymerizes so as to obtain melanin.

13 Claims, 7 Drawing Sheets
(6 of 7 Drawing Sheet(s) Filed in Color)

Relative fluoressence intensity (%)
100
80
60
40
20
0
Droplets
Surrounding phase
Dex
Y
Yox CN⁻ relative intensity
50
40
30
20
10
0
(ONB-Y)cl
(ONB-Y)cl-ox
Yox

METHODS AND COMPOSITIONS FOR MELANIN SYNTHESIS

CROSS REFERENCE TO RELATED APPLICATIONS

This application is a Bypass Continuation of PCT Patent Application No. PCT/IL2022/050003 having International filing date of Jan. 2, 2022, which claims the benefit of priority of U.S. Provisional Patent Application No. 63/134,789, filed Jan. 7, 2021, the contents of which are all incorporated herein by reference in their entirety.

BACKGROUND OF THE INVENTION

Melanin is a broad term for a group of natural pigments found in most organisms. Melanins are unique materials with remarkable properties including UV-protection, coloration and antioxidant activity. Melanin is produced through a multistage chemical process known as melanogenesis, where the oxidation of the amino acid tyrosine is followed by polymerization. The melanin pigments are produced in a specialized group of cells known as melanocytes.

There are three basic types of melanin: eumelanin, pheomelanin, and neuromelanin. The most common type is eumelanin. Pheomelanin is a cysteine-derivative that contains polybenzothiazine portions that are largely responsible for the colour of red hair, among other pigmentation. Neuromelanin is found in the brain.

In the human skin, melanogenesis is initiated by exposure to UV radiation, causing the skin to darken. Melanin is an effective absorbent of light; the pigment is able to dissipate over 99.9% of absorbed UV radiation. This property enables melanin to protect skin cells from UVB radiation damage, reducing the risk of folate depletion and dermal degradation, and it is considered that exposure to UV radiation is associated with increased risk of malignant melanoma. Melanin absorbs solar radiation and could be used to improve solar panels for energy harvesting.

The biosynthesis of melanin is highly regulated both spatially and temporally and involves supramolecular templating and compartmentalization of enzymes and reactants within specialized organelles called melanosomes.

In contrast, the laboratory-based synthesis of melanin is a poorly controlled process, resulting in materials with undefined properties.

There is, thus, a need for a developing methods and compositions for producing melanin-like materials.

SUMMARY OF THE INVENTION

In an embodiment of the invention, there is provided a composition comprising a polymer—based droplet, wherein the polymer—based droplet comprises melanin, a tyrosine substrate with a cleavable protecting group on the side chain, tyrosine, tyrosinase or any combination thereof.

In some embodiments, the polymer—based droplet is formed by phase separation.

In some embodiments, the polymer of the polymer—based droplet comprises dextran, PEG, polyelectrolytes with opposite charges i.e. poly-lysine, poly glutamic acid, polyarginine and poly-aspartic acid or any combination thereof.

In some embodiments, the polymers are PEG and Dextran and the amount of the polymers before phase separation is from 5-10 w/w % PEG and 10-20 w/w % dextran.

In some embodiments, the size of the droplet is between 100 nm to 200 μm.

In some embodiments, the polymer—based droplet is made according to the following steps: obtaining a solution of a tyrosine substrate with cleavable protecting group on the side chain (protected tyrosine) or a solution of unprotected tyrosine; obtaining a phase separation composition comprising two or more polymers or at least one polymer and a salt; and separating.

In some embodiments, the polymer—based droplet is made according to the following steps: obtaining a solution of tyrosine substrate with a cleavable protecting group on the side chain or a solution of tyrosine (protected tyrosine) or a solution of unprotected tyrosine; obtaining ATPS, PEG and dextran system by dissolving PEG and dextran in the protected or unprotected tyrosine solution; and separating.

In some embodiments, the droplet is a Dex rich droplet of PEG/Dex ATPS.

In some embodiments, the tyrosine substrate with a cleavable protecting group on the side chain is ortho-nitrobenzyl tyrosine (ONB-Y).

In some embodiments, there is provided a method of synthesizing melanin comprising the steps of: obtaining a polymer—based droplet containing a tyrosine substrate with a cleavable protecting group on the side chain (protected tyrosine) or a polymer—based droplet containing tyrosine (unprotected); adding tyrosinase; and if protected tyrosine is used cleaving the cleavable protecting group on the side chain of the tyrosine substrate with the cleavable protecting group on the side chain so as to obtain unprotected tyrosine; wherein the unprotected tyrosine is oxidized by tyrosinase and polymerizes so as to obtain melanin.

In some embodiments, the tyrosine substrate with a cleavable protecting group on the side chain is ortho-nitrobenzyl tyrosine (ONB-Y).

In some embodiments, the cleaving is by irradiation.

In some embodiments, the irradiation is by UV irradiation.

In some embodiments, the polymer is dextran, PEG, poly-lysine, poly glutamic acid.

In some embodiments, the melanin synthesis is a spatially-controlled synthesis.

In some embodiments, the droplet is a Dex rich droplet of PEG/Dex ATPS.

In some embodiments, the tyrosinase catalyses oxidation of the tyrosine into 3, 4-dihydroxyphenylalanine (DOPA), then to dopaquinone, followed by cyclization to cycloDOPA and polymerization and stacking of 5,6-dihydroxyindole (DHI) and 5,6-dihydroxyindole-2-carboxylic acid (DHICA) lead to the formation of eumelanin.

In some embodiments, there is provided a composition comprising the composition comprising a polymer—based droplet the invention and an acceptable carrier.

In some embodiments, the composition is a dermal composition or a cosmetic composition and comprises a dermally or cosmetically acceptable carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
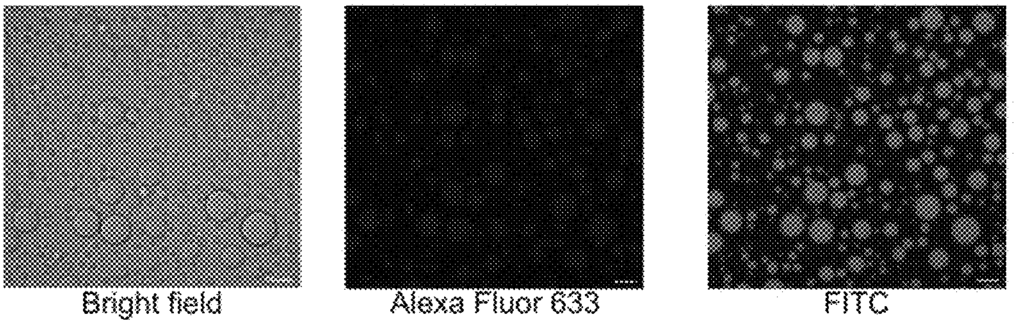
Figure 1B:
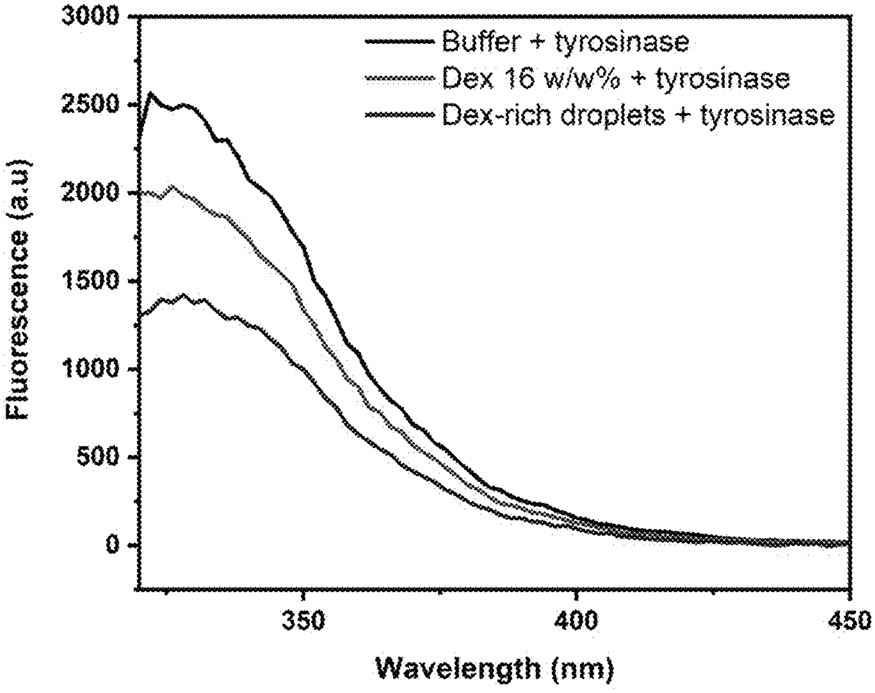

FIGS. 1A and 1B shows tyrosinase partitioning in Dex-rich droplets. FIG. 1A shows confocal microscopy images of FITC-labeled Dex (λex=488 nm) and Alexa 633-labeled tyrosinase (λex=633 nm), images are the middle section of z-stack, scale bars=20 μm. FIG. 1B shows bulk fluorescence measurement of tyrosinase fluorescence (by tryptophan fluorescence, λex=280 nm) in buffer, Dex 16 w/w % and Dex (ATPS).

Figure 2A:
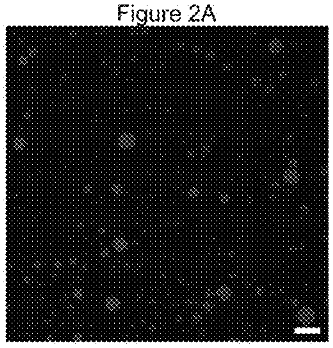
Figure 2B:
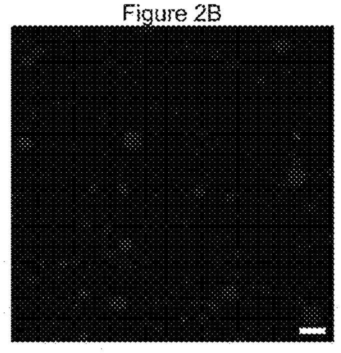
Figure 2C:
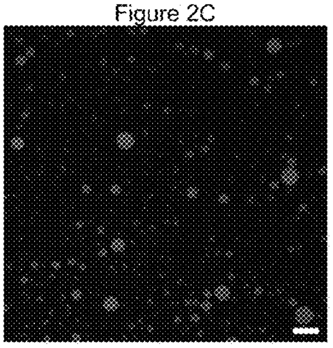
Figure 2D:
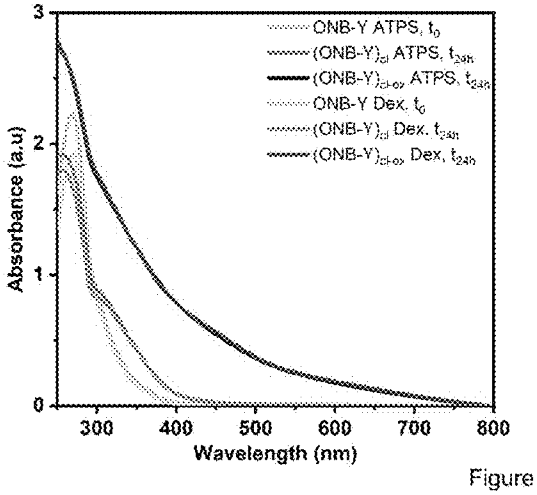
Figure 2E:
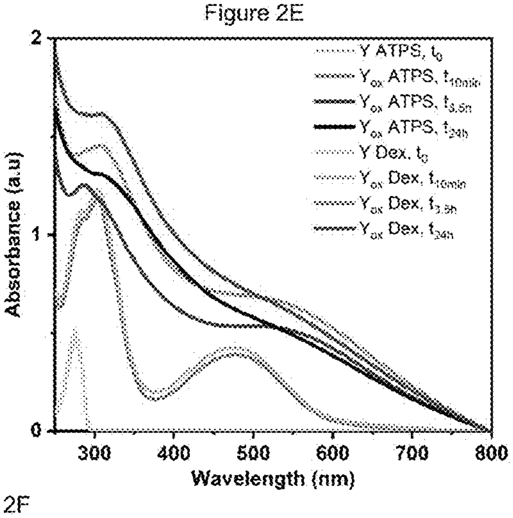
Figure 2F:
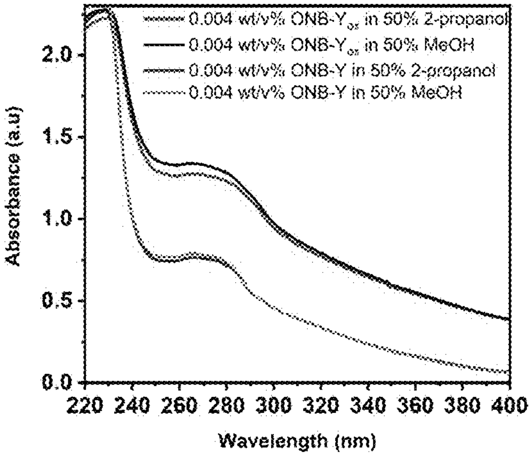

FIGS. 2A, 2B, 2C, 2D and 2E show Dex-rich droplets with ONB-Y and tyrosinase. FIGS. 2*a* and 2*b* shows optical microscopy images, at t=0 and t=25 h (respectively), scale bar 50 μm. FIGS. 2*c* and 2*d* show TEM micrographs at t=0 and t=(respectively), scale bar 200 nm. (t=0)—before UV-irradiation; (t=25 h)—after total from irradiation start (total irradiation time was 2 h). FIG. 2E shows UV-Vis absorbance spectra of ONB-Yox and Yox. FIG. 2F demonstrates UV-Vis absorbance spectra of ONB-Y and ONB-Yox in Dex-rich droplets. Samples were irradiated with UV for 2 h and incubated for another 22 h, then diluted in MeOH/2-propanol.

Figures 3A, 3B, 3C, 3D, 3E, 3F:
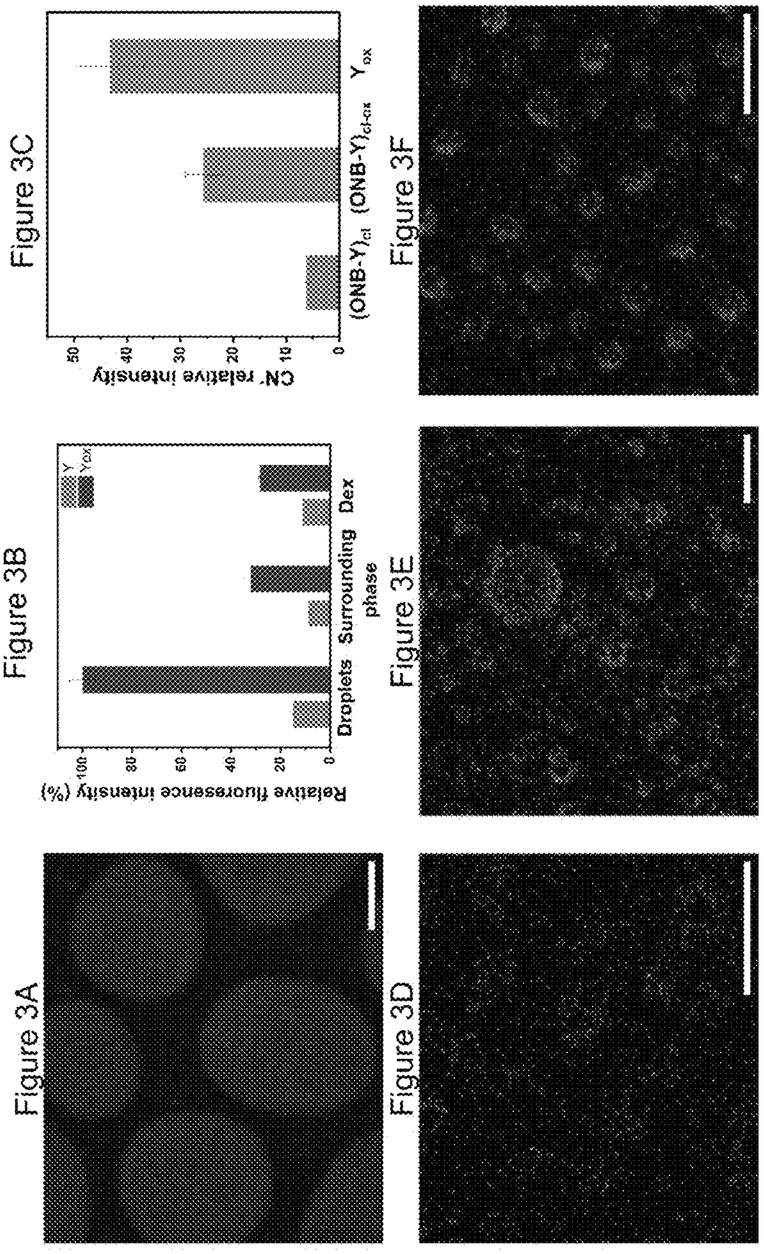

FIGS. 3A, 3B, 3C, 3D, 3E and 3F show melanin product formation in microdroplets. FIGS. 3A and 3B show confocal microscopy analysis of the intrinsic fluorescence of Yox melanin formed inside droplets (FIG. 3A), at the surrounding phase, or in homogenous Dex (FIG. 3B). Scale bar=20 μm. Fluorescence was measured at λex=405 nm, values represent average of relative intensity, n=27 for droplets or surrounding phase and n=18 for Dex. FIGS. 3C-3F show ToF-SIMS analysis of (ONB-Y)cl-ox and Yox in Dex-rich droplets. FIG. 3C show relative intensity of CN− ion of (ONB-Y)cl, (ONB-Y)cl-ox and Yox at t24 h in droplets. Samples were analyzed to obtain the normalized CN− ions intensity (normalized to O− ions) for particles obtained in the three samples. FIG. 3D-3F show chemical ion maps of CN− ions taken after sputtering at t24 h of (FIG. 3D) 1 mM (ONB-Y)cl, (FIG. 3E) 1 mM (ONB-Y)cl-ox and (FIG. 3F) 1 mM Yox. Scale bars=10 μm.

Figure 4B:
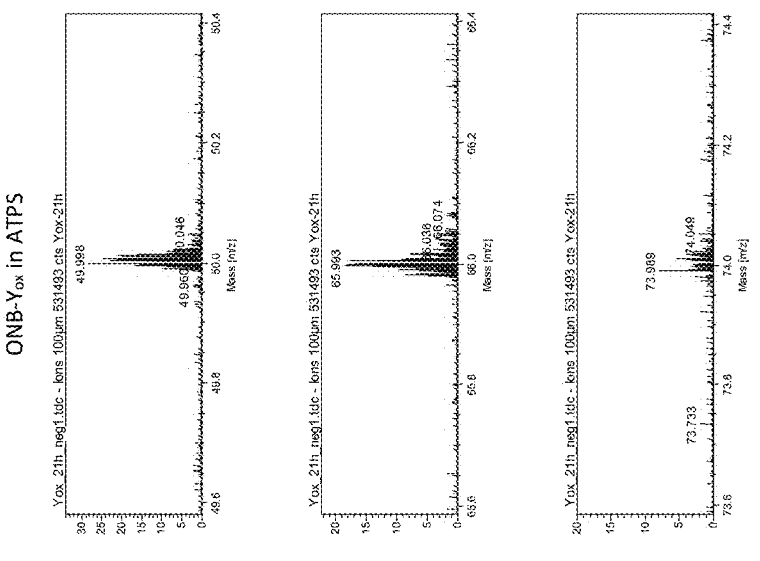
Figure 4A:
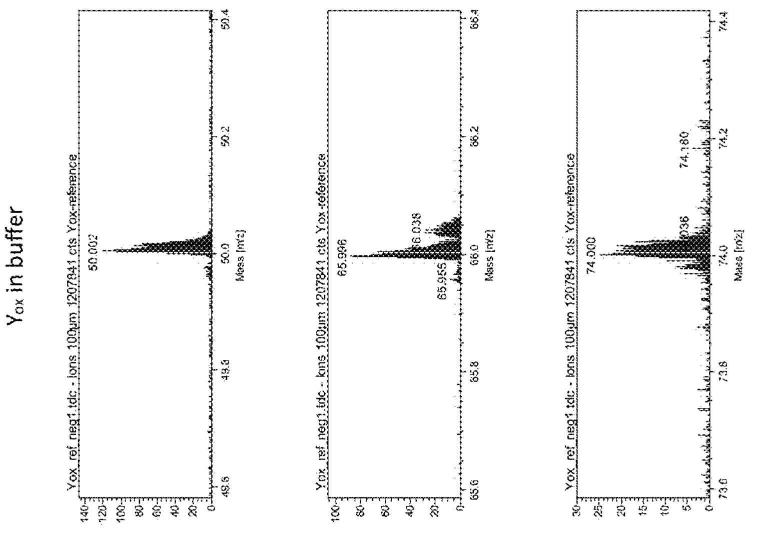
Figure 4D:
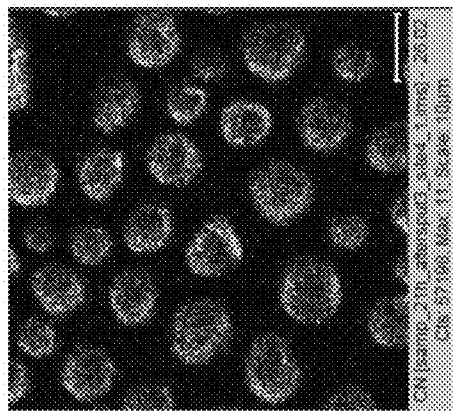
Figure 4C:
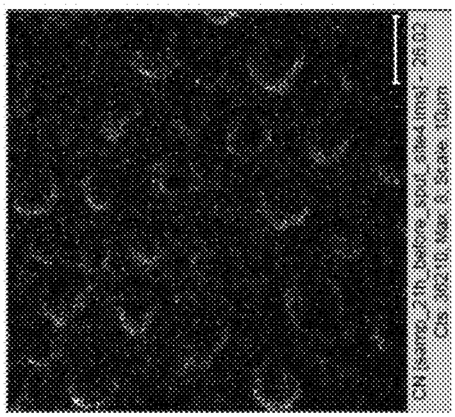

FIGS. 4A, 4B, 4C and 4D represent ToF-SIMS analyses of 1 mM Yox in buffer (FIG. 4A) and 1 mM ONB-Yox in Dex-rich droplets (FIG. 4B), indicating the eumelanin-characteristic peaks. FIGS. 4C and 4D show chemical ion maps of Dex-droplets of Yox (FIG. 4C) and ONB-Yox (FIG. 4D) sputtering, where the intensity of CN− ions inside the droplets is high.

Figure 5:
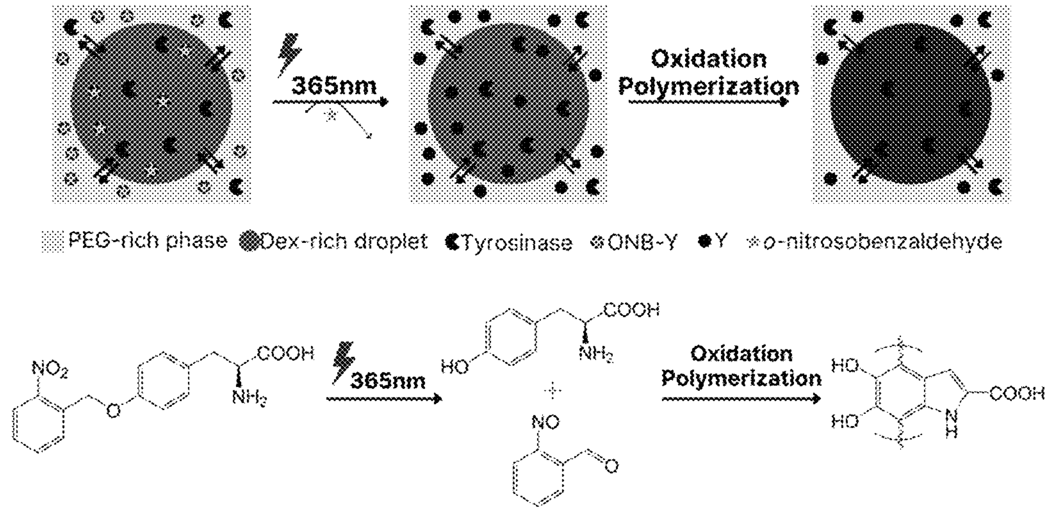

FIG. 5 shows schemes representing some exemplary embodiments of the designed system. At the top there is an illustration of ONB-Y and tyrosinase partitioning, ONB removal with UV irradiation, and free Y oxidized and polymerized into melanin particles. At the bottom, there is a chemical presentation of the ONB cleavage under UV irradiation, and free Y oxidized and polymerized into melanin particles.

Figures 6A, 6B, 6C, 6D:
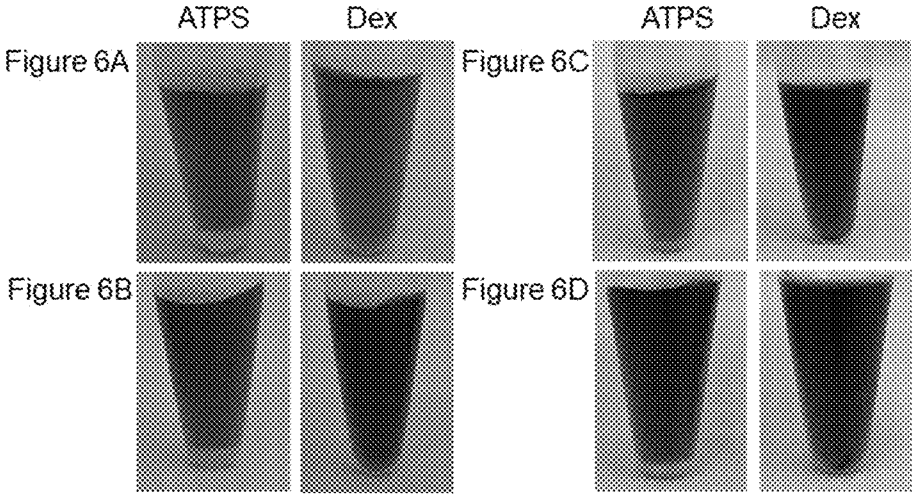

FIGS. 6A, 6B, 6C and 6D present macroscopic images of reaction mixtures in droplets (ATPS) compared to homogenous Dex following 24 h of oxidation and centrifugation FIG. 6A (ONB-Y)cl-ox; FIG. 6B Yox; FIG. 6C DAox; FIG. 6D. 10 mM of DA without tyrosinase.

DETAILED DESCRIPTION OF THE EMBODIMENTS OF THE INVENTION

The invention is based on the surprising findings that tyrosinase sequestration by the Dex-rich droplets allows for confined local reactivity, resulting in formation of soluble melanin in the compartments. Accumulation and compartmentalization of the melanin product in the droplets offers a tool to regulate the reactivity of the product. Briefly, the inventors have successfully designed a system for the spatiotemporal control of melanin synthesis. While most synthetic mimics of melanin composed of insoluble materials, the current system utilizes aqueous compartments to generate a water-soluble melanin. Due to the biocompatibility of its components and the photoprotective properties of the resulting material, this system has a tremendous technological potential in sun protection applications and can be readily formulated in skincare products. Moreover, this work suggests that the current method can be further developed to control the synthesis of additional insoluble biopolymers for various biotechnological applications.

Living cells are spatially ordered systems, where micro-compartmentalization is achieved by subcellular organelles. Melanins' biosynthesis is an example of the tremendous spatial and temporal control that is enabled by compartmentalization of enzymes and reactants within the cell. Human melanins and animal melanins are produced in specialized organelles called melanosomes that mature through four morphologically distinct stages. The first two stages are characterized by proteinaceous fibrils that are formed by the functional amyloid protein PMEL17. Melanin synthesis begins at stage III, where oxidized tyrosine is deposited on the pre-assembled fibrils, until internal structure is completely obscured at the end of stage IV. Unlike this ordered and controlled process, lab-based materials have ambiguous chemical structure and the regulation of the molecular morphology is complicated. The biosynthesis of the brown/black eumelanin, the most abundant form of melanin, involves tyrosinase-catalyzed oxidation of tyrosine into 3,4-dihydroxyphenylalanine (DOPA), then to dopaquinone, followed by cyclization to cycloDOPA and oxidation to DOPAchrome and eventually polymerization and stacking of 5,6-dihydroxyindole (DHI) and 5,6-dihydroxyindole-2-carboxylic acid (DHICA) lead to the formation of eumelanin (see scheme 1 below):

Scheme 1. Biosynthesis of eumelanin starting with tyrosine oxidation by tyrosinase

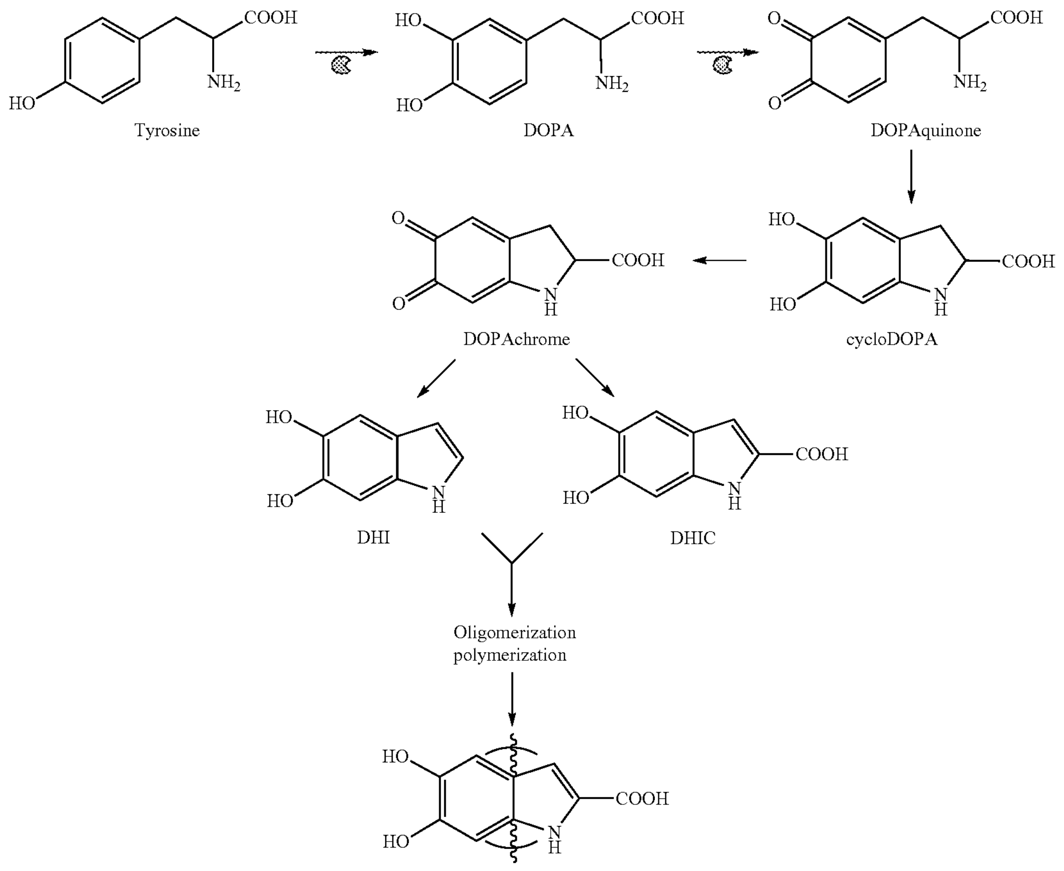

Tyrosine, DOPA, DOPAquinone, cycloDOPA, DOPAchrome, DHI, DHIC

Liquid—liquid phase separation (LLPS) is a common phenomenon in aqueous polymer solutions, which form by associative or non-associative (segregative) phase separation. Associative LLPS, or coacervation, results in a macromolecule-dense phase (coacervate) along with a dilute phase. In some embodiments of the invention, segregative phase separation is classically composed of two neutral polymers, or two polymers with opposite charge (polycationic and polyanionic polymers i.e. polylysine and polyaspartic acid or polyarginine and polyglutamic acid, or a polymer and a salt, creating different regions, each enriched in one of the components, and known as an aqueous two-phase system (ATPS). In an embodiment of the invention, the phase separation composition is ATPS that is based on polyethylene glycol (PEG) and dextran (Dex). These polymers also provide macromolecularly crowded aqueous compartments which mimic the cell milieu. Since these compartments are based on weak intermolecular interactions, they serve as 'open' reactors, where molecules can reversibly diffuse between the phases and serve as artificial microreactors and potentially use to control metabolic pathways. The partitioning of different solutes, such as, proteins and small molecules into one of the phases provide a mechanism for compartmentalization and localized reactivity.

In one exemplary embodiment of the invention, Dex-rich droplets of the PEG/Dex ATPS serve as liquid compartments, allowing the synthesis to occur in a confined space, similar to the spatially-controlled synthesis in vivo. In order to achieve a temporal control over the synthesis and maintain it exclusively inside the droplets, a protected tyrosine was used, such a protected tyrosine may be photocleavable or chemically cleavable. In one embodiment, as can be seen in FIG. 5, tyrosine substrate with photocleavable or chemically cleavable protecting group on the side chain may be used. Using a protected tyrosine enables control of melanin synthesis, resulting in synthetic melanin material.

Reference is made to FIG. 5 showing a system in which the Dex-rich droplets of the PEG/Dex ATPS serve as liquid compartments, allowing the synthesis to occur in a confined space, similar to melanins' spatially-controlled biosynthesis. In order to achieve a temporal control over the synthesis and maintain it exclusively inside the droplets, a Y substrate with photocleavable protecting group on the side chain (FIG. 5 upper panel). This system allows the control and confinement of tyrosine enzymatic oxidation, resulting in synthetic melanin material that can be readily applied in skincare applications.

The PEG/Dex ATPS system is used to spatially control melanin synthesis by compartmentalization and sequestration of Y and tyrosinase (FIG. 5 upper panel). To temporally control the enzymatic oxidation of Y into synthetic melanin, a side chain protected Y with the photocleavable group ortho-nitrobenzyl (ONB) was used, which is cleaved upon UV irradiation at 365 nm, allowing Y oxidation by tyrosinase (FIG. 5 bottom panel).

In some embodiments of the invention, there is provided a composition comprising a polymer—based droplet, wherein the polymer—based droplet comprises melanin, a tyrosine substrate with a cleavable protecting group on the side chain, tyrosine (also termed here free tyrosine or unprotected tyrosine), tyrosinase or any combination thereof.

In some embodiments, there is provided a composition comprising a polymer—based droplet, wherein the polymer—based droplet comprises melanin.

In some embodiments, there is provided a composition comprising a polymer—based droplet, wherein the polymer—based droplet comprises a tyrosine substrate with a cleavable protecting group on the side chain, tyrosinase or combination thereof.

In some embodiments, there is provided a composition comprising a polymer—based droplet, wherein the polymer—based droplet comprises tyrosine, tyrosinase or combination thereof.

The term "polymer—based droplet/s" (also termed here, "droplet" or "droplets") refers to liquid structures (droplets) comprising a condensed-phase polymer found within a dilute phase medium comprising a second polymer, or a salt. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located. In some embodiments, the droplet is formed by phase separation of a composition comprising two or more polymers or at least one polymer and a salt. The polymers may be a combination of polycations and polyanions. In some embodiments, the droplet is formed by obtaining a phase separation composition comprising two or more polymers or at least one polymer and a salt; and separating them by any method known in the art, such as without limitation, centrifugation. In some embodiments, the polymer may be a polysaccharide which is alginate, hyaluronic acid, chondroitin sulfate, dextran, dextran sulfate, heparin, heparin sulfate, heparan sulfate, chitosan, gellan gum, xanthan gum, guar gum, cellulose, carrageenan and any combination thereof. In some embodiments, the polymer is PEG, or two polyelectrolytes with an opposite charge i.e., poly-lysine, poly glutamic acid, poly-arginine and poly-glutamic acid, or poly(acrylic acid) (PAA) and poly(N,N-dimethylaminoethyl methacrylate) (PDMAEMA). In some embodiments, the composition comprises at least two polymers from any of the above-mentioned polymers. By tailoring the composition and the surface tension, 'active' droplets of sizes ranging from nanometres to hundreds of micrometres are formed. In some embodiments, the polymer—based droplet's are previously mixed with a solution comprising tyrosine or protected tyrosine or both so as to produce a composition comprising polymer—based droplet's containing tyrosine or protected tyrosine or both. In some embodiments, tyrosinase is added. In some embodiments, when melanin synthesis starts, the droplet may contain also melanin or any of the intermediates in the synthesis thereof as shown in Scheme 1.

According to some embodiments, the droplet is a Dex rich droplet of PEG/Dex ATPS.

According to some embodiments, the droplet is polymer is PEG, or two polyelectrolytes with an opposite charge i.e., poly-lysine, poly glutamic acid, poly-arginine and poly-glutamic acid, or poly (acrylic acid) (PAA) and poly (N,N-dimethylaminoethyl methacrylate) (PDMAEMA).

According to some embodiments, the size of the droplet is between 1000 nm to 20 μm.

According to some embodiments, the size of the droplet is between 100 nm to 200 μm.

According to some embodiments, the size of the droplet is between 50 nm to 400 μm.

According to some embodiments, the size of the droplet is between 5 nm to 400 μm.

According to some embodiments, the size of the droplet is between 5 nm to 200 μm.

In some embodiments the droplet composition of the invention is made according to the following steps: obtaining a solution of a tyrosine substrate with cleavable protecting group on the side chain (protected tyrosine) or a solution of unprotected tyrosine; obtaining a phase separation composition comprising two or more polymers or at least one polymer and a salt; and separating. In some embodiments, the droplet is made according to the following steps: obtaining a solution of tyrosine substrate with a cleavable protecting group on the side chain or a solution of tyrosine (protected tyrosine) or a solution of unprotected tyrosine; obtaining ATPS, PEG and dextran system by dissolving PEG and dextran in the protected or unprotected tyrosine solution; and separating. The step of separating can be done by any method that is available, such as centrifugation, removing by a pipette and the like.

In some embodiments the phase separation composition (i.e. before separation) contains between 2-20 w/w % PEG and between 5-30 w/w % dextran.

In some embodiments the phase separation composition contains between 1, 2, 3, 4, 5, 6, 7, 8, 9, 10, 11, 12, 13, 14, 15, 16, 17, 18, 19 or 20 w/w % PEG and between 5, 6, 7, 8, 9, 10, 11, 12, 13, 14, 15, 16, 17, 18, 19, 20, 21, 22, 23, 24, 25, 26, 27, 28, 29, or 30 w/w % dextran.

In some embodiments the phase separation composition contains between 5-10 w/w % PEG and between 10-20 w/w % dextran.

It is noted that the ratio between the two polymers in the phase separation is a function of the molecular weight (MW) of each of the polymers and the concentration thereof.

In some embodiments, the tyrosine is a protected tyrosine, wherein the cleavable protecting group on the side chain is photocleavable or is chemically cleavable, for example, by changes in the pH. In some embodiments, the protecting group is ortho-nitrobenzyl. In some embodiments, the protecting group is one or more of: Acetyl (Ac) Benzoyl (Bz), Benzyl (Bn), β-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl) diphenylmethyl] (MMT), p-Methoxybenzyl ether (PMB), p-Methoxyphenyl ether (PMP), Methylthiomethyl ether Pivaloyl (Piv), Tetrahydropyranyl (THP), Tetrahydrofuran (THF), Trityl (triphenylmethyl, Tr), Silyl ether, including trimethylsilyl (TMS), tert-butyldimethylsilyl (TBDMS), tri-iso-propylsilyloxymethyl (TOM), and triisopropylsilyl (TIPS) ethers), Methyl ethers, Ethoxyethyl ethers (EE), BOC glycine, Carbobenzyloxy (Cbz) group, p-Methoxybenzyl carbonyl (Moz or MeOZ) group, tert-Butyloxycarbonyl (BOC) group, 9-Fluorenylmethyloxycarbonyl (Fmoc) group, Acetyl (Ac) group, Benzoyl (Bz) group, Benzyl (Bn) group, Carbamate group, p-Methoxybenzyl (PMB), 3,4-Dimethoxybenzyl (DMPM), p-Methoxyphenyl (PMP) group, Tosyl (Ts) group, Troc (trichloroethyl chloroformate) group, Other Sulfonamides (Nosy) & Nps) groups, Acetals and Ketals, Acylals, Dithianes, Methyl esters, Benzyl esters, tert-Butyl esters, Esters of 2,6-disubstituted phenols (e.g. 2,6-dimethylphenol, 2,6-diisopropylphenol, 2,6-di-tert-butylphenol), Silyl esters, Orthoesters, Oxazoline, 2-cyanoethyl, Methyl (Me), Propargyl alcohols. Nitrobenzyl-based, carbonyl-based, benzyl-based photolabile protecting groups.

In some embodiments, there is provided a method for synthesizing melanin comprising the steps of: obtaining a polymer—based droplet containing a tyrosine substrate with a cleavable protecting group on the side chain (protected tyrosine) or a polymer—based droplet containing tyrosine (unprotected); adding tyrosinase; and if protected tyrosine is used a step of cleaving the cleavable protecting group on the side chain of the tyrosine substrate with the cleavable protecting group on the side chain is required so as to obtain unprotected tyrosine; wherein the unprotected tyrosine is oxidized by tyrosinase and is further polymerized so as to obtain melanin. In some embodiments, the cleaving is by irradiation. In some embodiments, the irradiation is a UV irradiation. In some embodiments, the cleaving is by changes in the pH. In some embodiments the tyrosine substrate with a cleavable protecting group on the side chain is ortho-nitrobenzyl tyrosine (ONB-Y) and the ONB is cleaved by irradiation as demonstrated in FIGS. 5A and 5B that demonstrate an exemplary embodiment of the invention with PEG/DEX ATPS system and a protected tyrosine ortho-nitrobenzyl tyrosine (ONB-Y).

In some embodiments, the protecting group may be Acetyl (Ac) Benzoyl (Bz), Benzyl (Bn), β-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl)diphenylmethyl] (MMT), p-Methoxybenzyl ether (PMB), p-Methoxyphenyl ether (PMP), Methylthiomethyl ether Pivaloyl (Piv), Tetrahydropyranyl (THP), Tetrahydrofuran (THF), Trityl (triphenylmethyl, Tr), Silyl ether, including trimethylsilyl (TMS), tert-butyldimethylsilyl (TBDMS), tri-iso-propylsilyloxymethyl (TOM), and triisopropylsilyl (TIPS) ethers), Methyl ethers, Ethoxyethyl ethers (EE), BOC glycine, Carbobenzyloxy (Cbz) group, p-Methoxybenzyl carbonyl (Moz or MeOZ) group, tert-Butyloxycarbonyl (BOC) group, 9-Fluorenylmethyloxycarbonyl (Fmoc) group, Acetyl (Ac) group, Benzoyl (Bz) group, Benzyl (Bn) group, Carbamate group, p-Methoxybenzyl (PMB), 3,4-Dimethoxybenzyl (DMPM), p-Methoxyphenyl (PMP) group, Tosyl (Ts) group, Troc (trichloroethyl chloroformate) group, Other Sulfonamides (Nosy) & Nps) groups, Acetals and Ketals, Acylals, Dithianes, Methyl esters, Benzyl esters, tert-Butyl esters, Esters of 2,6-disubstituted phenols (e.g. 2,6-dimethylphenol, 2,6-diisopropylphenol, 2,6-di-tert-butylphenol), Silyl esters, Orthoesters, Oxazoline, 2-cyanoethyl, Methyl (Me), Propargyl alcohols. Nitrobenzyl-based, carbonyl-based, benzyl-based photolabile protecting groups.

In some embodiments, the melanin synthesis of the invention is a spatially-controlled synthesis.

The melanin that is produced by the method and the droplets of the invention, may be used in skin care and skin health applications, such as, in sunscreen.

In some embodiments, if a protected tyrosine is used, it may be activated into an unprotected tyrosine gradually over time, so that the composition will continue to synthesize melanin over time. For example, the irradiation may take place for more than one time for a short period each time and hence the melanin synthesis will continue over time. This would enable active melanin synthesis for a long time and may be used for example in a sunscreen or when antioxidant activity of the composition is need for a long time.

In some embodiments, there is provided a composition comprising the composition comprising a polymer—based droplet, wherein the polymer—based droplet comprises melanin, a tyrosine substrate with a cleavable protecting group on the side chain, tyrosine (also termed here free tyrosine or unprotected tyrosine), tyrosinase or any combination thereof and an acceptable carrier.

In some embodiments, the composition is a dermal composition or a cosmetic composition and comprises a dermally or cosmetically acceptable carrier.

In some embodiments, the composition is a sunscreen composition comprises a dermally or cosmetically acceptable carrier.

In some embodiments, the composition is used for coloration and comprises acceptable additives.

In some embodiments, the composition is used for coloration and comprises acceptable additives.

In some embodiments, the composition is used as antioxidant composition and comprises acceptable additives.

EXAMPLES

The examples show a temporal control was achieved over the synthesis by using a protected tyrosine, such as, ortho-nitrobenzyl tyrosine (ONB-Y), which enables the tyrosine to react with tyrosinase only upon cleavage of the ONB moiety. A system was designed for analysis of tyrosinase partitioning into a phase separation composition, such as, Dex-rich droplets of ATPS in order to gain spatial control over melanin synthesis.

Methods and Materials

Experimental Section

Materials o-(2-Nitrobenzyl)-L-tyrosine hydrochloride, sodium phosphate monobasic and sodium phosphate dibasic were purchased from Holland Moran. Thermo Fisher Scientific Alexa Fluor™ 633 Protein Labeling Kit was purchased from Rhenium. PEG 8 kDa, dextran 10 kDa, fluorescein isothiocyanate (FITC)-Dex 10 kDa conjugate, L-tyrosine and tyrosinase (isolated from *Agaricus bisporus*) were purchased from Sigma-Aldrich. Water, acetonitrile and trifluoroacetic acid (HPLC grade) were purchased from Bio-Lab.

ONB-Y and Y sample preparation.

ONB-Y stock solution was prepared by dissolving ONB-Y in DMSO (2%) and 50 mM (or 5 mM) phosphate buffer at pH 8 and sonicating for 4-8 h, followed by filtration. The same procedure was used for preparation of Y stock solution.

Formation of PEG/Dex ATPS:

ATPS composition was based on previous studies. ATPS stocks were prepared at 10 w/w % 8 kDa PEG and 16 w/w % 10 kDa Dex. PEG/Dex were dissolved in 1 mM ONB-Y stock solution (or in 50 mM phosphate buffer at pH 8). Buffer was manually prepared in-house using a combination of sodium phosphate monobasic and sodium phosphate dibasic. ATPS was centrifuged to separate the two phases, and then the upper PEG-rich phase was removed via pipette. The same procedure was used for L-tyrosine (Y). Homogenous Dex solution was prepared by dissolving 16 w/w % 10 kDa Dex in a substrate stock solution, or in 50 mM phosphate buffer.

ONB-Y Cleavage Kinetics:

o-(2-Nitrobenzyl)-L-tyrosine hydrochloride (ONB-Y) was dissolved to 1.3 mM in double distilled water (ddw). The sample was irradiated in a UV box (λ=365 nm, 6 Watt) for 180 min. Samples were taken for HPLC analysis every 15 min. Samples were analyzed using analytical highperformance liquid chromatography (HPLC) on a Dionex SD Ultimate 3000 UHPLC standard system equipped with a Diode-Array Detection (DAD) Detector. Mobile phases were (A) $H_2O$ (0.1% TFA) and (B) MeCN (0.1% TFA). Separation conditions for all the samples were as follows: Analytical Hypersil GOLD RP-C18 Column (from Thermo Fisher) 175 Å 1.9 μm 50×2.1 mm with a flow rate of 0.6 ml/min. Gradient was as follows: $H_2O$/MeCN 0 min [90/10], 0-2.500 min [45/55], 2.500-3.000 min [10/90], 3.000-3.250 min [10/90], 3.250-5.000 min [90/10]. Samples were analyzed at λ=214 nm.

Tyrosine Oxidation in Droplets:

Tyrosinase was dissolved at 3.5 mg/ml in 50 mM phosphate buffer at pH 8 and diluted 10-fold in the Dex-rich droplets solution (final concentration of 0.35 mg/ml). The sample was transferred into 96 multi-well plate and irradiated (λ=365 nm, 6 Watt) in a UV-box for 2 h.

Tyrosine Oxidation in Bulk:

Tyrosinase was dissolved at 3.5 mg/ml in 50 mM (or 5 mM) phosphate buffer at pH 8 and diluted 10-fold in each sample (final concentration of 0.35 mg/ml). The sample was transferred into a 96 multi-well plate and irradiated (λ=365 nm, 6 Watt) in a UV-box for 2 h. After irradiation, the sample was analyzed every few hours by UV-Vis absorbance measurements and imaged by confocal microscopy (150 μl sample) and transmission electron microscopy.

UV-Vis Absorbance Measurements:

UV-Vis absorbance spectra of oxidized ONB-Y, Y, or DA in ATPS and homogenous Dex were taken using Synergy H1 microplate reader, between 230-800 nm (every 5 nm), after 30 sec of shaking before each measurement. DAox was prepared by dissolving 1 mM DA in DMSO (2%) and 50 mM phosphate buffer at pH 8, then tyrosinase was dissolved at 3.5 mg/ml in 50 mM phosphate buffer at pH 8 and diluted 10-fold in the (final concentration of 0.35 mg/ml). Sepia melanin solution was prepared by dissolving 0.6 mg/ml of Sepia melanin (Sigma) in 1 M NaOH with 4% DMSO. After 10 h of bath sonication the solution was diluted by 50% v/v % 100 mM phosphate buffer. The pH was adjusted to a value of 10 by adding 1 M HCl solution and then 100 mM phosphate buffer to receive a final Sepia melanin concentration of mg/ml (equivalent to the concentration of Y in the oxidation experiments). Background subtraction have been performed for each sample (control and unoxidized samples were not diluted).

Confocal Microscopy Analysis:

Samples were directly imaged from a multi-well plate, using a ZEISS LSM 900 inverted confocal microscopy with 10× or ×20/0.8 NA Plan-Apochromat objective. Images were collected and processed using Zen software (Zeiss). Bright field images were obtained by PMT channel. Fluorescence images were taken using 640 nm and 488 nm lasers (for Alexa Fluor 633 and FITC, respectively).

Confocal Microscopy Analysis of Tyrosinase Sequestration:

Labeling: Tyrosinase was labeled at amines using succinimidyl ester functionalized Alexa Fluor 633 labeling kit (Invitrogen). The labelled enzyme was purified using a gel filtration column. Partitioning: labelled tyrosinase was diluted 1:5 (final concentration of 0.09 mg/ml) in an ATPS prepared with FITC-Dex. ATPS were prepared with 0.02% FITC-Dex, 10 w/w % PEG 8 kDa and 15.98 w/w % Dex 10 kDa ATPS in 50 mM phosphate buffer at pH 8. After 18 h of incubation, 40 μl of the sample was transferred into an imaging multi-well plate. The fluorescence intensity was averaged from 12 μm circles, 48 droplets and 48 background points were analyzed to obtain a fluorescence intensity profile to evaluate tyrosinase partitioning in the Dex-rich droplets. Tyrosinase uptake by the Dex-rich droplets was calculated from the average fluorescence intensity values of Alexa Fluor 633 as described in equation 1.

$$\text{Tyrosinase uptake} = \frac{\text{Fluoresence intensity inside the droplets}}{\text{Fluoresence intensity at the background}}. \quad \text{Equation 1}$$

Partitioning of Y, ONB-Y and Tyrosinase in ATPS

Y: Absorbance measurements of different Y concentration in 2% DMSO in phosphate buffer have been performed to obtain a calibration curve (λ=275 nm). Partitioning evaluation of 1 mM Y solution was performed by dissolving 10 w/w % 8 kDa PEG and 16 w/w % 10 kDa Dex in 1 mM Y. The ATPS was centrifuged and each phase was collected, and centrifuged again (repeated twice for each phase). The concentration of Y in each phase was calculated after subtraction of the background (PEG or Dex separated in the same manner, which were dissolved in 2% DMSO in 50 mM phosphate buffer) of each sample. ONB-Y: The same procedure was used for ONB-Y, with the exception of using lower concentrations for the calibration curve measurements (due to high absorbance values, λ=269 nm), and 0.4 mM ONB-Y solution was used for the partitioning experiment. Tyrosinase: For the calibration curve (λ=280 nm), different tyrosinase concentration were prepared in 50 mM phosphate buffer, and diluted 10-fold in each phase separately (ATPS dissolved in 2% DMSO in 50 mM phosphate buffer, separated as described for Y). Absorbance measurements and background subtraction was done as described for Y. Partitioning evaluation was performed by dissolving 5 mg/ml tyrosinase in 50 mM phosphate buffer and diluted 10-fold in ATPS dissolved in 2% DMSO in 50 mM phosphate buffer (final concentration of 0.5 mg/ml). The ATPS was mixed by rotation for 2 h. Then the phases were separated as described for Y, and concentration in each phase was determined. All partitioning coefficients, K, were calculated from the average concentrations of each phase as described in equation 2.

$$K = \frac{C_{PEG}}{C_{Dex}}. \quad \text{Equation 2}$$

Transmission Electron Microscopy:

10 μl of the sample solution were applied to a carbon-coated grid and incubated for 2 mins. Excess solution was removed by blotting the grid with a piece of filter paper, followed by staining with 10 μl of 2% (w/v) uranyl acetate solution for 2 min. After blotting excess stain solution, the grid was left to air dry. The negatively stained sample was imaged in a JEM-1400Plus TEM operating at 80 kV. Images were recorded using SIS Megaview III camera, iTEM the Tem imaging platform (Olympus).

Quantification of Tyrosine Oxidation Using Confocal Microscopy:

Unoxidized samples were diluted (10% dilution with 50 mM phosphate buffer). Samples containing 1 mM Y or $Y_{ox}$ were directly imaged from a multi-well plate using a ZEISS LSM 900 inverted confocal microscopy with 405 nm laser. Images were collected and processed using the Zen software (Zeiss). The histograms were stretched from the lower 30% of the original histogram. The fluorescence intensity was averaged from 30 μm circles. The number of sampled droplets and spots outside the droplets (in the surrounding phase) is n=27 for the ATPS samples and n=18 for the homogeneous Dex samples. Values were normalized to percentage.

Time-of-Flight Secondary Ion Mass Spectrometry:

The sample was diluted 10-fold in ddw. 10 μl of the diluted sample were applied to a silicon chip and left air-dried in a desiccator overnight. ToF-SIMS data acquisition was performed using a TRIFT II instrument (Physical Electronics, USA). For high mass resolution spectroscopy, the instrument employed a 15 KeV $Ga^+$ ion source. The 600 pA dc primary ion beam was pulsed at 10 kHz frequency with a pulse width of 15 ns. During high spatial resolution imaging, the instrument employed the $Ga^+$ source at 25 keV, 60 pA dc current and 30 ns pulses. A low-energy electron beam was used for charge compensation. For sputtering purpose, a 500 eV $Cs^+$ ion gun with 50 nA current was used. The sputtering was applied in order to see a possible melanin content inside the polymer particles. Negative ions of $CN^-$ were diagnostic for melanin inside the polymer particles and used to image the melanin distribution. For the particles without melanin, the $CN^-$ ions intensity was low and similar to the surrounding area, while the particles with melanin were highlighted with the $CN^-$ ions. Negative ions of $O^-$ and $CHO_2^-$ were representative for the PEG and Dex polymers, significantly highlighting the particles on ion images. Both these ions were used for normalization of $CN^-$ signal to compare between samples and showed similar results. In order to exclude impact of $CN^-$ background between the particles, a retrospective data analysis was applied. During acquisition of mass spectra and images, all data were saved in RAW data files, so that after finishing the analysis, it was possible to use a "region of interest" option. Inside the whole analysis area, the particles only areas were specified, and mass spectra were extracted from the particles only. Three areas of each sample were analyzed. In order to compare between the different analyzed samples in 5 mM phosphate buffer, the intensity of the relevant peaks was normalized by total counts. Three or four areas of each sample were analyzed.

Example 1

ANALYSIS of the Necessary UV Irradiation Time, as Derived from the Protected Tyrosine Cleavage Kinetics, and Tyrosinase Partitioning into an Exemplary Phase Separation System.

A methodology to spatiotemporally control melanin synthesis was developed in dynamic melanosome-inspired PEG/Dex protocells. In this system, the Dex-rich droplets of the PEG/Dex ATPS serve as liquid compartments, allowing the synthesis to occur in a confined space, similar to melanins' spatially-controlled biosynthesis. In order to achieve a temporal control over the synthesis and maintain it exclusively inside the droplets, a Y substrate with photocleavable protecting group on the side chain (FIG. 1) has been used. This system allows the control and confinement of tyrosine enzymatic oxidation, resulting in synthetic melanin material that can be readily applied in skincare applications.

The PEG/Dex ATPS system to was used to spatially control melanin synthesis by compartmentalization and sequestration of Y and tyrosinase (FIG. 1*a*). To temporally control the enzymatic oxidation of Y into synthetic melanin, side chain protected Y was used with the photocleavable group ortho-nitrobenzyl (ONB), which is cleaved upon UV irradiation at 365 nm, allowing Y oxidation by tyrosinase (FIG. 1*b*). ONB cleavage following UV irradiation by HPLC was used. This analysis showed that >90% of the ONB is cleaved after 180 min of UV irradiation (not shown).

To sequester tyrosinase within liquid droplets, PEG/Dex ATPS was obtained by dissolving PEG and Dex in. We utilized the PEG/Dex ATPS system to spatially control melanin synthesis by compartmentalization and sequestration of Y and tyrosinase (FIG. 1*a*). To temporally control the enzymatic oxidation of Y into synthetic melanin, we used side chain protected Y with the photocleavable group ortho-nitrobenzyl (ONB), which is cleaved upon UV irradiation at 365 nm, allowing Y oxidation by tyrosinase (FIG. 1*b*). We first analyzed ONB cleavage following UV irradiation by HPLC. This analysis showed that >90% of the ONB is cleaved after 180 min of UV irradiation (not shown).

To sequester tyrosinase within liquid droplets, PEG/Dex ATPS was obtained by dissolving PEG and Dex in ONB-Y or Y solution, and collecting the upper PEG-rich phase containing Dex-rich droplets, which were previously shown to efficiently sequester various proteins and enzymes. 2 Dex droplets were formed directly upon ATPS preparation, dispersed in the continuous PEG-rich phase. Notably, in the absence of PEG no droplets are formed by a dilute Dex solution. Tyrosinase (0.35 mg/ml) was added directly to the Dex-rich droplets in the PEG-rich phase. The reaction was UV irradiated for 120 min as no significant difference was observed between 120 and 180 min of irradiation (not shown) and analyzed by various spectroscopy and microscopy techniques. Following ONB cleavage [(ONB-Y)cl] and oxidation [(ONB-Y)cl-ox)] in the droplets, an evident color change to dark brown was observed not shown). The liquid droplets before and after melanin synthesis by using transmission electron (TEM) and optical microscopy were analyzed. The microscopy analyses showed that droplet diameter widely ranging from 200 nm (not shown) up to 150 μm after oxidation due to coalescence (not shown).

Example 2

Melanin Synthesis in the Droplets

Upon ATPS preparation with 1 mM ONB-Y, the two phases were separated by centrifugation, followed by PEG-rich phase removal via pipette. Dex-rich phase droplets are formed directly upon ATPS preparation, dispersed in the continuous PEG-rich phase. Tyrosinase was added to the Dex-rich phase droplets and the sample was inserted to a UV box and was irradiated for 2 h under UV-light (λ=365 nm.

As shown in FIG. 2*a*, the droplets fluoresce intensely upon excitation at λex=488 nm as a result of the FITC-labeled Dex, confirming that they are indeed Dex-rich, where PEG is found in the continuous phase. In addition, the droplets clearly fluoresce upon excitation at λex=640 nm (FIGS. 2*b*-2*c*), indicating that the labeled tyrosinase partitions in the Dex-rich droplets. Quantitative analysis of the droplets' fluorescence showed a 8.9-fold increase in tyrosinase uptake by the Dex-rich droplets compared to the PEG phase (not shown). A similar value was previously reported for urease uptake by Dex droplets in a PEG/Dex ATPS.

To analyze the optical properties of the melanin formed in the microdroplets, a UV-Vis spectroscopy analysis of ONB-Y and Y oxidation in droplets (ATPS) compared with reaction in homogenous Dex was conducted. The λmax of ONB-Y shifted from 269 nm to 260 nm following cleavage of the protecting group [(ONB-Y)cl] (FIG. 2*d*). The UV-Vis spectra of the cleaved and oxidized ONB-Y [(ONB-Y)cl-ox] showed intense absorption in the UVB-UVA (280-400 nm) region and broadening in the visible range (400-750 nm) at t24 h of oxidation, typical for eumelanin and melanin-like materials. No significant difference was observed between the absorbance of the (ONB-Y)cl-ox product formed in ATPS compared to homogenous Dex (FIG. 2*d*). In contrast, higher absorbance intensity was observed for melanin formed by oxidation of unprotected Y (Yox) in homogenous Dex compared to ATPS at t24 h (FIG. 2*e*). Monitoring the UV-Vis absorbance of the two reactions showed the emergence of λmax=300 nm peak, attributed to dopachrome formation. At t3.5 h, this absorbance peak redshifts in the Yox Dex reaction and has higher intensity compared to Yox ATPS. At t24 h, the two reaction mixtures absorb broadly across the UV and visible light. Moreover, (ONB-Y)cl-ox exhibits higher absorbance intensity in the UVB-UVA region whilst Yox absorbs more intensely in the visible range. Similar results were observed for (ONB-Y)cl-ox and Yox in bulk phosphate buffer at pH 8 (not shown). The UV-Vis absorbance of melanin formed by enzymatic oxidation of dopamine (DAox) in droplets or homogenous Dex or Sepia melanin in Dex showed typical monotonic broad absorption between 250 nm-800 nm (not shown). Macroscopic images of the DAox melanin materials formed in droplets compared to homogenous Dex (FIG. 6*c*) showed higher solubility of the reaction mixture in droplets, where reaction in bulk Dex resulted in formation of black precipitation (FIG. 6*c*). A similar trend was observed following spontaneous oxidation of DA (10 mM) in droplets compared to bulk Dex (FIG. 6*d*), suggesting that accumulation of the melanin product in droplets prevents its aggregation and precipitation.

In addition, the UV-Vis absorbance of the crude product in organic solvents was measured (FIG. 2F). 24 h after the beginning of the reaction, the sample was dissolved in 50% 2-propanol or 50% MeOH, to give final concentration of 0.004 wt/v % (for more details please see Supporting Information). These results are similar to the measured absorbance of commercial sunscreens.

Next, melanin's intrinsic fluorescence to monitor product formation within droplets by using confocal microscopy was used, which allows for a spatial resolution analysis of liquid samples. While the fluorescent signal of (ONB-Y)cl-ox was too weak to be monitored by confocal microscopy (not shown), the droplets containing Yox fluoresced after 24 h of oxidation at λex=405 nm as a result of melanin formation (FIG. 3*a*). The fluorescence intensity of Yox melanin within droplets was >3-fold higher than that in the surrounding phase (FIG. 3*b*), indicating that the melanin product is accumulated and compartmentalized within the droplets. This compartmentalization provides a means to control and regulate melanin reactivity in complex mixtures. Similarly, one of the functionalities attributed to melanosomes is the compartmentalization and storage of melanin to prevent the reaction of the pigment with cellular biomolecules, which might have a pathological outcome.

In addition, the resulting melanin material in the droplets at a spatial resolution was chemically analyzed by using time-of-flight secondary ion mass spectrometry (ToF-SIMS). This methodology provides identification and mapping of molecules and chemical structures at high spatial resolution. The biosynthesis of the brown/black eumelanin involves oxidation of tyrosine into 3,4-dihydroxyphenylalanine (DOPA), then to dopaquinone, followed by spontaneous cyclization to cycloDOPA and eventually polymerization and stacking of 5,6-dihydroxyindole (DHI) and 5,6-dihydroxyindole-2-carboxylic acid (DHICA) to eumelanin (not shown). Masses of ions that were previously reported as characteristic for eumelanin, including C3N—, C3NO—, and C5N-,27,28 could be detected only in bulk oxidation reactions, presumably due to interference of signal from ions of the PEG/Dex system. Yet, these masses are not indicative for Y oxidation-polymerization as they also appear in samples of unoxidized ONB-Y before and after cleavage (not shown), suggesting a similar fragmentation pattern of the ONB group and the oxidized species. Depth profiling of the droplets using sputtering of the samples' surface showed an increase in the intensity of CN− ions inside droplets containing either (ONB-Y)cl-ox or Yox (FIG. 3*c-f*). This analysis suggests that the increase in CN− ions observed following oxidation for both (ONB-Y)cl-ox and Yox is due to formation of new bonds during the oxidation-polymerization process and that the reaction mainly occurs inside the droplets. The higher intensity of CN− ions in Yox might be related to the increased accessibility of the free Y for tyrosinase oxidation compared to that of ONB-Y.

In order to achieve a better understanding of the chemical characteristics of the obtained melanin-like product, time-of-flight secondary ion mass spectrometry (ToF-SIMS) analyses were performed. This technique provides identification and mapping of molecules and chemical structures at high spatial resolution. The eumelanin-characteristic peaks (C3N—, C3NO— and C5N—) were detected in samples of oxidized ONB-Y (ONB-Yox) and oxidized tyrosine (Yox, serves as reference) as shown in FIG. 4*a-b*. Moreover, sputtering of the ONB-Yox surface reveals significantly higher intensity of CN— ions inside the droplets (FIG. 4*c-d*), as a result of the melanin-like product content of the droplets.

In summary, the examples provide a successfully designed a system for the spatiotemporal controlled melanin synthesis. This is achieved by using Dex-rich droplets or any other droplets to sequester the tyrosinase, which create a confined space for the reaction. Temporal control is achieved by using UV cleavable protected substrate, so the oxidation may occur mainly inside the droplets. The system was characterized by UV-Vis spectroscopy, microscopy and mass spectrometry, indicating the presence of the desired melanin-like material. The simplicity of the system, together with the photoprotective properties of the material set this system as a promising potential product in various skin health applications.

In order to achieve a better understanding of the chemical characteristics of the obtained melanin-like product, time-of-flight secondary ion mass spectrometry (ToF-SIMS) analyses were performed. This technique provides identification and mapping of molecules and chemical structures at high spatial resolution. The eumelanin-characteristic peaks (C3N—, C3NO— and C5N—) were detected in samples of oxidized ONB-Y (ONB-Yox) and oxidized tyrosine (Yox, serves as reference) as shown in FIG. 4*a-b*. Moreover, sputtering of the ONB-Yox surface reveals significantly higher intensity of CN− ions inside the droplets (FIG. 4*c-d*), as a result of the melanin-like product content of the droplets While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A composition comprising a polyethylene glycol (PEG)/dextran aqueous two-phase system (ATPS) comprising a PEG rich continuous phase and dextran-rich droplets dispersed in the PEG-rich continuous phase, wherein:

the dextran-rich droplets comprise a tyrosinase and a tyrosine substrate optionally protected with a cleavable protecting group on a side chain;

the ATPS is based on 5-10 w/w % PEG and 10-20 w/w % dextran;

the continuous PEG-rich phase comprises a higher concentration of PEG than of dextran and the dextran-rich droplets comprise a higher concentration of dextran than of PEG;

the tyrosine substrate and the tyrosinase preferentially partition into the dextran-rich droplets; and when the tyrosine is unprotected, the unprotected tyrosine is enzymatically oxidized by the tyrosinase to form melanin within the dextran-rich droplets.

2. The composition of claim 1, wherein the cleavable protecting group on a side chain of the tyrosine is photocleavable or chemically cleavable.

3. The composition of claim 1, wherein the protected tyrosine is ortho-nitrobenzyl tyrosine (ONB-Y).

4. The composition of claim 1, wherein the size of the droplet is between 100 nm to 200 μm.

5. The composition of claim 1, wherein the composition is a dermal composition or a cosmetic composition and comprises a dermally or cosmetically acceptable carrier.

6. The composition of claim 1, wherein the dextran has a molecular weight of about 10 kDa.

7. The composition of claim 6, wherein the PEG has a molecular weight of about 8 kDa.

8. The composition of claim 1, wherein the tyrosinase is enriched in the droplets by at least 5-fold compared to the continuous phase.

9. The composition of claim 1, wherein the melanin formed in the dextran-rich droplets exhibits reduced aggregation relative to melanin formed in a homogeneous aqueous phase.

10. A method of synthesizing melanin comprising the steps of:

preparing an aqueous two-phase system (ATPS) by dissolving 5-10 w/w % polyethylene glycol (PEG) and 10-20 w/w % dextran in an aqueous solution comprising a tyrosine substrate optionally protected with a cleavable protecting group on a side chain;

centrifuging the ATPS to create an upper and a lower phase;

collecting the upper phase comprising dextran-rich droplets dispersed in a PEG-rich continuous phase;

adding tyrosinase to the collected upper phase; and waiting for the appearance of a dark brown color, indicating that the tyrosine substrate was enzymatically oxidized by the tyrosinase to form melanin within the dextran-rich droplets, wherein:

if protected tyrosine is used, the method further comprises, following the addition of the tyrosinase, a step of cleaving the cleavable protecting group on the side chain of the protected tyrosine so as to obtain unprotected tyrosine;

the PEG-rich continuous phase comprises a higher concentration of PEG than of dextran and the dextran-rich droplets comprise a higher concentration of dextran than of PEG; and the tyrosine substrate and the tyrosinase preferentially partition into the droplets.

11. The method of claim 10, wherein the protected tyrosine is ortho-nitrobenzyl tyrosine (ONB-Y).

12. The method of claim 10, wherein the cleaving is by irradiation.

13. The method of claim 10, wherein the irradiation is by UV irradiation.

* * * * *